(12) United States Patent
Friesen et al.

(10) Patent No.: US 11,039,941 B2
(45) Date of Patent: Jun. 22, 2021

(54) PROSTHETIC FOOT

(71) Applicant: OTTO BOCK HEALTHCARE GMBH, Duderstadt (DE)

(72) Inventors: Jeff Friesen, Salt Lake City, UT (US); Justin R. Smith, West Jordan, UT (US); Oleg Pianykh, Salt Lake City, UT (US)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 178 days.

(21) Appl. No.: 15/309,290

(22) PCT Filed: May 8, 2015

(86) PCT No.: PCT/DE2015/100190
§ 371 (c)(1),
(2) Date: Nov. 7, 2016

(87) PCT Pub. No.: WO2015/169291
PCT Pub. Date: Nov. 12, 2015

(65) Prior Publication Data
US 2017/0135828 A1 May 18, 2017

(30) Foreign Application Priority Data
May 9, 2014 (DE) .................. 102014006687.8

(51) Int. Cl.
*A61F 2/66* (2006.01)
*A61F 2/50* (2006.01)

(52) U.S. Cl.
CPC ........ *A61F 2/66* (2013.01); *A61F 2002/5001* (2013.01); *A61F 2002/5003* (2013.01);
(Continued)

(58) Field of Classification Search
CPC ................ A61F 2/66; A61F 2002/5001; A61F 2002/6657
See application file for complete search history.

(56) References Cited

U.S. PATENT DOCUMENTS 3,890,650 A 6/1975 Prahl
4,506,395 A 3/1985 Haupt
(Continued)

FOREIGN PATENT DOCUMENTS

CA 2103341 A1 4/1995
CN 1061713 A 6/1992
(Continued)

OTHER PUBLICATIONS

PCT International Search Report for PCT International Patent Application PCT/DE2015/100190, dated Aug. 25, 2015.

*Primary Examiner* — Bruce E Snow
(74) *Attorney, Agent, or Firm* — Holland & Hart LLP

(57) ABSTRACT

A prosthetic foot, comprising a core, on which a proximal fastening device for fastening the prosthetic foot to a lower-leg tube or to a lower-leg shaft is arranged and which is surrounded by a foot casing. The foot casing forms a cavity, in which the core is inserted. A slot-shaped recess is formed in a front foot region of the foot casing, into which slot-shaped recess a tongue arranged on the core is inserted. The front foot region has a stiffness that deviates in comparison with the rest of the foot casing.

31 Claims, 3 Drawing Sheets

(52) U.S. Cl.
CPC ............... *A61F 2002/5007* (2013.01); *A61F 2002/6657* (2013.01)

(56) References Cited

U.S. PATENT DOCUMENTS

| | | | |
|---|---|---|---|
| 4,865,612 A * | 9/1989 | Arbogast | A61F 2/66 623/55 |
| 4,892,554 A | 1/1990 | Robinson | |
| 5,007,938 A | 4/1991 | Prahl | |
| 5,156,632 A | 10/1992 | Wellershaus | |
| 5,219,365 A * | 6/1993 | Sabolich | A61F 2/66 623/53 |
| 5,443,522 A | 8/1995 | Hiemisch | |
| 5,888,239 A * | 3/1999 | Wellershaus | A61F 2/66 623/47 |
| 5,897,594 A | 4/1999 | Martin et al. | |
| 6,053,946 A | 4/2000 | Wilkinson | |
| 6,596,029 B1 | 7/2003 | Gramnas | |
| 6,811,571 B1 | 11/2004 | Phillips | |
| 8,128,709 B2 | 3/2012 | Thorhallsdottir et al. | |
| 2002/0040249 A1 | 4/2002 | Phillips | |
| 2003/0045944 A1 | 3/2003 | Mosler et al. | |
| 2003/0093158 A1 | 5/2003 | Phillips et al. | |
| 2005/0071018 A1 | 3/2005 | Phillips et al. | |
| 2013/0144403 A1 | 6/2013 | Lecomte et al. | |
| 2013/0173023 A1 | 7/2013 | Lecomte et al. | |

FOREIGN PATENT DOCUMENTS

| | | |
|---|---|---|
| CN | 1078880 A | 12/1993 |
| CN | 1395479 A | 2/2003 |
| CN | 1529573 A1 | 9/2004 |
| DE | 4038063 A1 | 6/1992 |
| DE | 9315665 U1 | 12/1993 |
| DE | 19521147 C1 | 12/1996 |
| EP | 0487852 A1 | 6/1992 |
| EP | 0793949 A1 | 9/1997 |
| JP | S60-18165 A | 1/1985 |
| JP | H1-500403 | 2/1989 |
| JP | H4-285551 | 10/1992 |
| JP | 2003-518961 | 6/2003 |
| RU | 2112466 C1 | 6/1998 |
| WO | 88/00815 | 2/1988 |

* cited by examiner

PROSTHETIC FOOT

TECHNICAL FIELD

The invention relates to a prosthetic foot comprising a core, on which a proximal fastening device for securing the prosthetic foot to a below knee tube or a below knee shank is arranged and which is surrounded by a foot casing which forms a cavity into which the core has been inserted.

BACKGROUND

Prosthetic feet are the distal terminations of prosthetic devices of the lower extremity and fastened either directly to a below knee shank, or else to a below knee tube, which in turn is fastened to a prosthetic knee joint. Prosthetic feet can have very different designs and satisfy very different problems. In addition to the highly complex, driven prosthetic feet, which have an ankle joint, there are multi-part spring structures which should assist the user in enabling a gait which approximates the natural gait behavior as closely as possible. Prosthetic feet with a comparatively simple setup are the so-called SACH feet, which have a solid ankle joint and a cushioned heel. Such a prosthetic foot may have a wooden core, which has a foam casing foamed therearound. The prosthetic foot reproduces the outer form of a natural foot, with different foot sizes existing, into which form cores of different dimensions can be inserted.

U.S. Pat. No. 8,128,709 B2 relates to a functional foot cover, in which foot casing, into which a prosthetic foot insert has been inserted, is provided. The prosthetic foot has a base spring and, arranged thereon in an articulated manner, an ankle element which is able to be fastened to a below knee tube. The prosthetic foot casing has zones with different elasticity in the sole region in order, firstly, to dampen the heel strike when the prosthetic foot strikes and, secondly, to return energy when rolling over the forefoot in order to influence the gait behavior as desired. The material inserts in the foot casing can be arranged or formed both on the outer side and on the inner side. The roll-over behavior is decisively determined by way of the base spring of the prosthetic foot insert.

SUMMARY

It is an object of the present invention to provide a prosthetic foot which can be produced in a cheap and modular manner and by means of which an adaptation of the foot properties can be carried out in a cost-effective manner.

US 2005/0071018 A1 relates to a prosthetic foot with an ankle block, at the upper end of which fastening elements are fastened for attaching the prosthetic foot to a below knee tube. A sole plate made out of a stable, flexible material is fastened to the underside of the ankle block. The sole plate and the ankle block are surrounded by a foot cosmesis, which is arranged in the front and rear region of the sole plate. A strengthening element is arranged in the toe region.

According to the invention, this object is achieved by a prosthetic foot having the features of the main claim. Advantageous refinements and developments of the invention are disclosed in the dependent claims, the description and the figures.

The prosthetic foot comprising a core, on which a proximal fastening device for securing the prosthetic foot to a below knee tube or a below knee shank is arranged and which is surrounded by a foot casing which forms a cavity into which the core has been inserted, provides for a separate receiving portion with a slot-shaped recess to be formed in a forefoot region of the foot casing, with a tongue arranged on the core being inserted into said recess.

As a result of securing the core in a form-fitted manner by way of the separate receiving portion, with the tongue inserted therein, in the forefoot region, it is possible to influence the foot function as desired. The foot function substantially includes the heel behavior, the roll-over behavior and the forefoot behavior. The heel behavior and the roll-over behavior up to the mid-stance phase are determined by the deformation behavior of the core, to the extent that the latter is deformable, and by a possibly present heel spring or by the elastic behavior of the foot casing. The forefoot behavior and the roll-over behavior from the mid-stance phase onward are determined, in turn, by the core and the elastic properties of the foot casing in the forefoot region. By way of the form-fit connection of the front part of the core, which is embodied in the form of a tongue, has a tongue-shaped projection or has a tongue fastened to it, it is possible to influence the properties, in particular the effective foot length, by varying the foot casing, the core, the receiving portion or the tongue. Here, the effective foot length is the distance between the force transmission points during the roll-over, while the prosthetic foot is on the ground with both the heel and the forefoot. The effective foot length is changed by the rigidity in the forefoot region. If the forefoot region is softer, the prosthetic foot behaves like a short prosthetic foot with a rigid forefoot region; if a harder or stiffer forefoot region is set, there is an increase in the effective foot length, and the prosthetic foot therefore behaves like a comparatively longer prosthetic foot. The tongue is inserted into the slot in the receiving portion, so that the forefoot region may have deviating rigidity in relation to the remaining foot casing, into which the tongue or the receiving portion has not been inserted.

The receiving portion enables an adjustable hardness of the forefoot without a change in the overall foot casing form or material composition of the foot casing becoming necessary. The embodiment of the receiving portion as a separate element brings about a material separation of foot casing and core such that tensions in the region of the ball of the foot are reduced. The foot casing and the receiving portion may be embodied from foam material. By separating the two foam materials which, in particular, are coupled to one another with form fit, there is a reduction in the mechanical load and an increase in the longevity of the foot casing and the receiving portion. Moreover, it is possible to realize different foot sizes using only one foot module or core and different foot casings by virtue of the receiving portion being interchanged and adapted to the respective foot size.

The separate design of foot casing and receiving portion renders it possible to set different levels of hardness of the forefoot by virtue of different materials being used. This results in a reduction in weight since the foot casing and the receiving portion are produced separately from one another and able to be selected in a manner adapted to the function. In general, the foot casing needs to have greater mechanical stability in relation to friction or wear-and-tear than the receiving portion; by contrast, the receiving portion must be easily adjustable in respect of the desired hardness or deformability. The materials which are ideal for the respective requirements are generally different and can be selected in a manner optimized in view of the densities thereof such that this results in a reduction of weight in comparison with an integral foot casing or an integral core.

The receiving portion enlarges the abutment face of the core within the foot casing such that this reduces tension peaks and increases the longevity of the foot casing.

Belts or rigid materials such as plastic or metal plates may be arranged in the foot casing or the receiving portion, in particular foamed in, in order to enable a possibly desired extension of the forefoot during pushoff.

The recess for receiving the tongue is formed in the receiving portion, which in turn may be embodied in a manner filling out the forefoot region of the foot casing. The receiving portion, and hence of forefoot region of the foot casing, are therefore completely filled with material, into which a slot has been inserted or formed. A sufficient mechanical rigidity of the foot casing is obtained by way of the receiving portion, and so forces may be transferred from the tongue to the foot casing by way of the receiving portion, with the foot casing forming the outer termination of the prosthetic foot and having a form approximated to that of the natural foot. The foot casing is advantageously made of an elastic plastics material, in particular a foamed material, which has sufficient rigidity for receiving and transferring the forces, a sufficient resistance to wear-and-tear, and the desired elastic and optical properties. Therefore, the forefoot region of the foot casing has a solid embodiment and holds the tongue of the core.

The forefoot region and/or receiving portion may either consist of the same material as the remaining foot casing, or it is likewise possible for the forefoot region and/or the receiving portion to have a rigidity that deviates from the remaining foot casing, as a result of which it is possible to achieve an adaptation of the forefoot rigidity and of the elastic behavior of the foot casing to the patient or to the desired properties of the prosthetic foot. As a result, it is possible for foot casings of the same size to be equipped with cores which are structurally the same but to have different rollover behaviors, for example by virtue of the receiving portions being equipped with different rigidities. The receiving portion may be inserted into the foot casing and held there by frictional forces, adhesive forces or form-fit elements. Preferably, the receiving portion has a replaceable embodiment or an embodiment which is removable from the foot casing in order to be able to carry out a simple adaptability to the respective requirements. It is likewise possible for the receiving portion to be formed into the foot casing, or formed thereon, for example within the scope of the primary shaping method when molding or injection molding the foot casing. As a complement to the insertion, or as an alternative thereto, it is possible for the receiving portion to be adhesively bonded in the foot casing. Initially, the receiving portion is manufactured from a material with the desired elastic and mechanical properties and the remaining foot casing with the cavity for receiving the core is subsequently formed thereon or, conversely, the receiving portion is molded into the cavity.

Advantageously, the core is inserted into the foot casing in an interchangeable manner and has a removable design. Preferably, the core is held in the foot casing and/or the receiving portion purely by form fit, supported by the frictional forces which occur due to the material properties of the foot casing or of the receiving portion. To this end, form-fit elements are provided on the core and corresponding form-fit elements are provided at the foot casing, particularly in the heel region, for example in the form of grooves and projections or undercuts, into which corresponding form-fit elements of the respective other component engage such that the foot casing can easily be secured to the core in an interchangeable and form-fit manner. The same can also be formed for the receiving portion in the foot casing and the tongue in the receiving portion.

The core may comprise a leaf spring, the front end of which forms the tongue. It is likewise possible for the tongue to be fastened to the core, with the tongue projecting beyond the front end of the core. The tongue is therefore fastened to the core as a separate component. It is also possible for the leaf spring to form the core such that the tongue can be fastened to the leaf spring as a core as a separate component. As a result of the embodiment of the core as a leaf spring or as a result of equipping the core with a leaf spring, it is possible to further differentiate the rollover behavior and to provide additional elasticity, which goes beyond the elasticity of the foot casing. As a result, it is possible to achieve an improved adaptation to the natural rollover behavior.

The core may have a heel cushioning, which consists of a foam which, in addition to elastic properties, also provides damping. It is also possible for a heel spring to be provided, the damping behavior of which is generally different from the damping behavior of a foam body.

The tongue may be embodied as a belt or leaf spring, wherein a high-strength fabric with adequate rigidity may be provided as belt material. It is possible to form the tongue into the receiving portion and subsequently secure it to the core, when the latter is inserted into the cavity. It is likewise possible to position the tongue in the foot casing together with the separately embodied receiving portion during the insertion together with the core and to secure it there.

A belt or a leaf spring can be integrated into the receiving portion and/or into the foot casing in order to provide a complementary adjustment possibility in respect of the rigidity of the foot casing or foot cosmesis.

The tongue is advantageously fastened to the underside of the core, i.e. to that side which faces the sole or the floor. In order to obtain maximal influencing of the rollover behavior, provision is advantageously made for the tongue to project into the toe region, wherein provision can be made for the tongue to have a width which varies over the length thereof in order to obtain an adaptation to the foot form and the geometric conditions. By way of example, if the tongue is only intended to project into the front big-toe region, it is necessary to reduce the width. In principle, it is also possible for the tongue to have a multipart design or for it to let itself be spread such that one part of the tongue extends into the big-toe region and another part extends in the remaining toe region.

The foot casing or foot cosmesis can have a stiffening in the midfoot region, also in addition to the tongue, which stiffening extends into the forefoot region in order to allow the respectively desired stiffness of the foot casing, and hence also of the entire prosthetic foot, to be set as desired.

One variant of the invention provides for a separate insertion element with a rigidity deviating from the foot casing or the receiving portion to be arranged in the forefoot region, for example in the foot casing or else in a receiving portion, in order to be able to embody the foot casing as a functional component. As a result of the insertion element, it is possible to adapt the foot casing itself in terms of the rigidity thereof, for example by virtue of the insertion element being fastened within the foot casing or the receiving portion in an interchangeable manner. The receiving element can be inserted, adhesively bonded into the receiving portion or into the casing or it can be inserted, adhesively bonded or formed to remain permanently within the foot casing, the receiving portion, but in any case in the forefoot region.

The stiffening is advantageously embodied in such a way that, during the terminal stance phase in the rollover procedure, the force introduction point shifts in the anterior direction in order to increase the effective foot length.

In addition to an embodiment of the prosthetic foot with a separate receiving portion, the forefoot region of the foot casing may have a slot-shaped recess, into which a tongue arranged on the core has been inserted, wherein the forefoot region has a deviating rigidity in comparison with the remaining foot casing. The forefoot region may have a solid embodiment.

BRIEF DESCRIPTION OF THE DRAWINGS

Exemplary embodiments of the invention are explained in more detail below on the basis of the attached figures. In detail.

DETAILED DESCRIPTION

Figure 1:
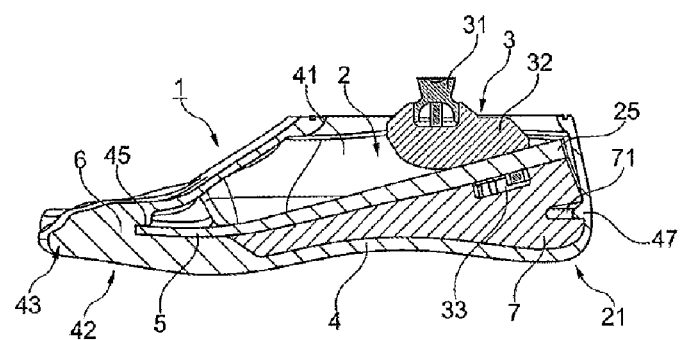
FIG. 1 shows a schematic cross-sectional view of a prosthetic foot.

FIG. 1 depicts, in a schematic sectional illustration, a prosthetic foot 1 with a core 2, which is fastened a proximal fastening device 3 with a screw-in pylon 31 and a fastening adapter 32 by way of screws 33. The fastening adapter 32 is fastened to the core 2 in an interchangeable manner in order to enable an adaptability to different users, heel heights, shoe forms or the like. The core 2 has a leaf spring 25, on the top side of which the fastening device 3 is fastened. Heel cushioning 7 made of a foam material is arranged on the lower side of the leaf spring 25, i.e. on the side which is directed to the sole or to the floor. In the depicted exemplary embodiment, the heel cushioning 7 is adhesively bonded to the leaf spring which consists of a fiber-reinforced plastics material, for example a carbon fiber reinforced plastic. The top side of the heel cushioning 7 is adhesively bonded over the whole area thereof to the lower side of the leaf spring 25; recesses are provided for the screw 33 or the screws 33 for fastening the fastening adapter 32. A groove 71 is formed in the heel cushioning 7 in the heel region 21 of the prosthetic foot 1, with a projection 47, which is formed on the inner side of the foot casing 4, engaging in said groove and securing the heel region of the foot casing 4 with form fit to the heel region 21 of the core 2.

The foot casing 4, which is made of a foam material, forms a cavity 41, into which the core 2, which consists of the leaf spring 25 and the heel cushioning 7 in the depicted exemplary embodiment, is inserted. In the forefoot region 42 of the foot casing 4 there is a receiving portion 6, in which a slot-shaped recess 45 is formed. The front end of the leaf spring 25, which is embodied as a tongue 5 and which projects beyond the front end of the heel cushioning 7, engages into this slot-shaped recess 45. The tongue reaches from the region of the metatarsophalangeal joint into the mid-toe region 43 and holds the core 2 in the forefoot region 42 of the foot casing 4 with form-fit. The receiving portion 6 is completely filled with the material of the remaining foot casing 4 and provides sufficient mechanical stability to transfer forces from the prosthetic foot user to the floor in the case of a load on the forefoot. As a result of the form-fit and interchangeable configuration of the fastening of the core 2 within the foot casing 4 by way of the tongue 5 and the slot-shaped recess 45, it is possible to permit a relative movement during a deformation of the elastic foot casing 4 and the leaf spring 25 during the rollover process such that only a small shearing load is generated within the foot casing 4.

Figure 2:
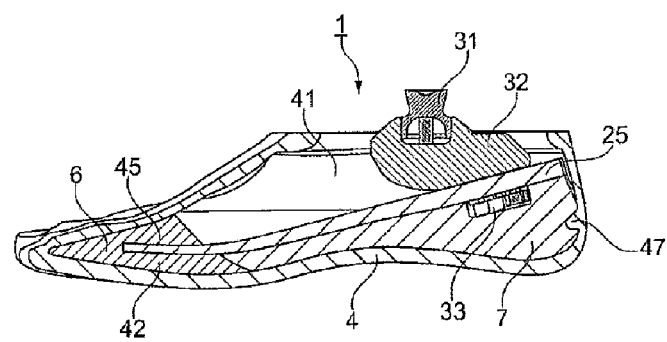
FIG. 2 shows a variant with a modified receiving portion.

FIG. 2 shows a variant of the invention in accordance with FIG. 1, in which a separate receiving portion 6 is arranged within the foot casing 4 instead of an integral configuration of the foot casing 4 with the receiving portion 6. The receiving portion 6 may be formed on, adhesively bonded to, or held with form fit on the remaining foot casing 4. The receiving portion 6 has a rigidity and elasticity behavior which differs from the behavior of the remaining foot casing 4 such that a change in the elastic behavior of the prosthetic foot 1 may be obtained by the separate receiving portion 6 or the receiving portion 6 made of a different material, which was formed therein or thereon. The receiving portion 6 extends into the front toe region 43, and so the entire length of the prosthetic foot 1 may be used to influence the gait behavior. The more rigid the receiving portion 6, the larger the effective foot length, the softer the receiving portion 6, the shorter the effective foot length. The separate receiving portion 6 can be inserted into the cavity 41 of the foot casing 4 together with the core 2 during the final assembly of the prosthetic foot 1. It is likewise possible for the separate receiving portion 6 to be initially inserted into the foot casing 4 and for it to be secured there with form fit, force fit or in a cohesive manner. Subsequently, the tongue 5, as a front part of the leaf spring 25, is inserted into the recess 45 in order to bring about mechanical locking of the tongue 5, and hence of the core 2, in the cavity 41 of the foot casing 1 together with the form-fit connection in the heel region 21 by way of the groove 71 and the projection 47.

Figure 3:
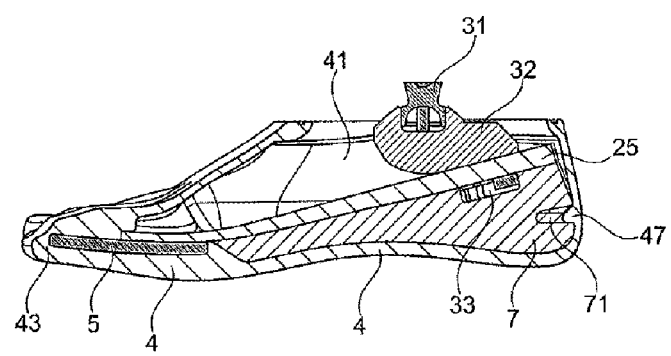
FIG. 3 shows a variant with a separate tongue.

A further variant of the invention is depicted in FIG. 3, in which the setup in principle corresponds to that of FIG. 1 such that reference is fully made thereto. A separate tongue 5 which projects into the front toe region 43 of the foot casing 4 is arranged on the lower side of the leaf spring 25 in the forefoot region 42. The separate tongue 5 may be embodied as a leaf spring with a deviating spring constant in relation to the leaf spring 25 of the core 2; it is likewise possible for the tongue 5 to be embodied as belt, band or other insertion part, which is arranged on the lower side of the leaf spring 25 and secured there. By way of example, securing may be brought about by adhesive bonding, welding or by mechanical fastening means such as screws, rivets, clips or the like. The embodiment with a separate tongue is advantageous in that the variability for configuring and setting the prosthetic foot may be increased in a simple and cost-effective manner.

Figure 4:
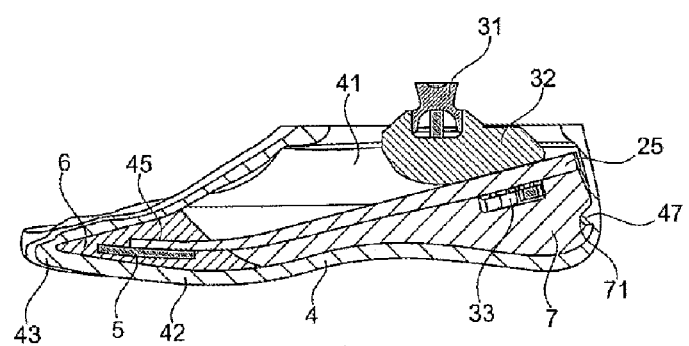
FIG. 4 shows a variant in accordance with FIG. 2 with a separate tongue.

FIG. 4 shows the variant in accordance with FIG. 2 with a separate tongue 5. The force-transmitting connection between the separate tongues 5 and the respective core 2 or the leaf spring 25 enables the effective foot length to be set. Here, the effective foot length can be lengthened into the front toe region, and so a maximum effective foot length can be obtained.

In the exemplary embodiments, the core 2 is embodied as a spring element 25 made of a carbon fiber composite component with heel cushioning 7. The heel cushioning 7 decisively influences the properties of the prosthetic foot 1 from the heel strike to a mid-stance phase. The heel cushioning 7 extends over approximately ⅔ of the entire foot length from the heel in the direction of the forefoot. The length of the heel cushioning 7 approximately corresponds to 75% of the length of the leaf spring 25. The fastening device 3 and the core 2 made of leaf spring 25 and heel cushioning 7 provide a foot module which, in turn, is inserted into a correspondingly embodied cavity 41 of a foot casing and held therein by means of form-fit elements 71, 47, 45, 5. The connection between the foot casing 4 and the foot module is not permanent; rather, the foot casing 4 is detachably fastened to the foot module. The foot casing 4 may consist of a foam material or else have various foam materials. The foam materials can have different densities and hardnesses; it is likewise possible for foam materials which only differ in regions thereof or the same foam materials to have different hardness and density.

It is possible to influence the effective foot length by controlling the hardness of the foot casing 4 or of the receiving portion 6 in the forefoot region.

Figure 5:
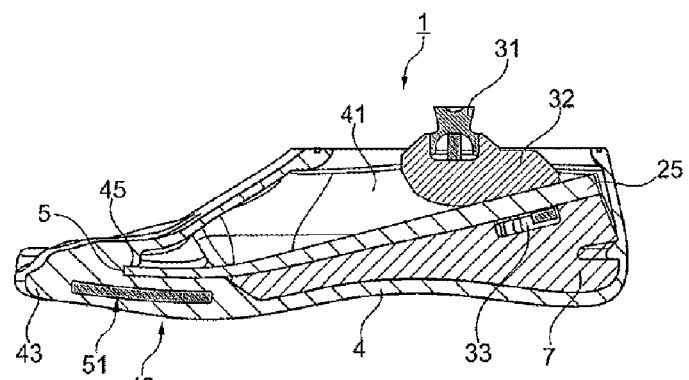
FIG. 5 shows a variant of FIG. 1 with a separate insertion element.

FIG. 5 depicts a schematic illustration of a variant of FIG. 1, in which a separate insertion element 51 (also referred to as a stiffening or stiffening feature 51), which extends as far as the toe region 43, is inserted into the forefoot region 42. The insertion element 51 may be embodied as leaf spring, belt or foam element with a rigidity which differs from the rigidity of the material in the forefoot region 42, in particular in the filled-out front forefoot region 42, in order thus to be able to influence the effective foot length in interaction with the leaf spring 25. In the depicted exemplary embodiment, the insertion element 51 is foamed in; alternatively, it can be inserted in an interchangeably fastened manner or adhesively bonded.

Figure 6:
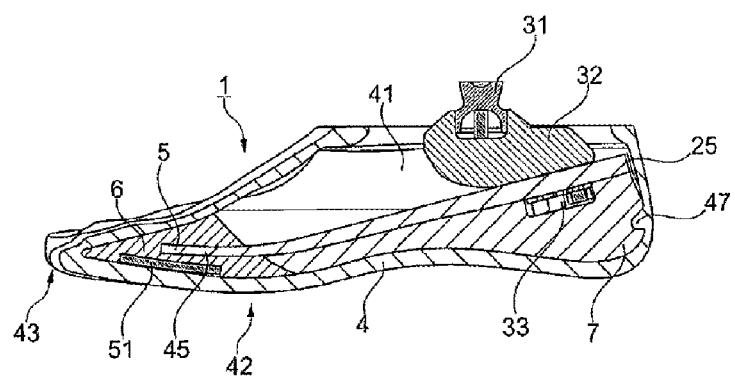
FIG. 6 shows a variant of FIG. 5.

A further variant is shown in FIG. 6, wherein the separate insertion element 51 is arranged on the lower side of the receiving portion 6. The insertion element can be exchangeably inserted or adhesively bonded into a recess within the receiving portion 6 and subsequently be covered by the foot casing and securely held on the receiving portion 6. It is likewise possible for the insertion element 51 to be formed thereon or formed therein, wherein the materials, and hence also the rigidity of the insertion element 51, are selected on the basis of what elastic properties are intended to be obtained in the forefoot region 42 and what effective foot length is intended to be set by means of the insertion element 51. The insertion element 51 projects beyond the front tip of the tongue 5, and hence also beyond the front tip of the leaf spring 25. It is also possible for the separate insertion element 51 to find use in conjunction with a separate tongue 5, as is shown in FIGS. 3 and 4.

The invention claimed is:

1. A prosthetic foot, comprising:
   a core comprising a leaf spring and a heel cushion, the leaf spring having a top side, a bottom side, and a frontal end portion, the heel cushion positioned along the bottom side of the leaf spring, the leaf spring projecting in an anterior direction from the heel cushion;
   a proximal fastening device configured to secure the prosthetic foot to a below knee tube or a below knee shank;
   a receiving portion having a pre-formed slot-shaped recess sized to removably receive the frontal end portion of the leaf spring to permit interchanging of the receiving portion relative to the core, the receiving portion extending anteriorly beyond the frontal end portion of the leaf spring;
   a foot casing having a cavity, the core and the receiving portion being insertable into and removable from the cavity to permit interchanging of the core and receiving portion relative to the foot casing.

2. The prosthetic foot as claimed in claim 1, wherein the cavity of the foot casing includes a forefoot region, and the receiving portion fills the forefoot region.

3. The prosthetic foot as claimed in claim 1, wherein the receiving portion comprises a material with a different stiffness than material of the foot casing.

4. The prosthetic foot as claimed in claim 1, wherein the core is secured to the foot casing in a heel region of the core with at least one form fit element.

5. The prosthetic foot as claimed in claim 1, further comprising a tongue arranged on the leaf spring or established by the leaf spring, the tongue being inserted into the slot-shaped recess, wherein the tongue is fastened to the leaf spring and projects beyond the frontal end portion of the leaf spring.

6. The prosthetic foot as claimed in claim 1, wherein the heel cushion protrudes at its frontal end from the leaf spring.

7. The prosthetic foot as claimed in claim 6, wherein a frontal end of the heel cushion establishing an inclined surface or an arcuate surface abutting on a rear surface of the receiving portion.

8. The prosthetic foot as claimed in claim 1, further comprising a tongue arranged on the leaf spring or established by the leaf spring, the tongue being inserted into the slot-shaped recess, wherein the tongue comprises a belt spring or a leaf spring.

9. The prosthetic foot as claimed in claim 1, wherein a belt spring or a leaf spring is integrated into at least one of the receiving portion and the foot casing.

10. The prosthetic foot as claimed in claim 1, further comprising a tongue arranged on the leaf spring or established by the leaf spring, the tongue being inserted into the slot-shaped recess, wherein the tongue is fastened to a lower side of the leaf spring.

11. The prosthetic foot as claimed in claim 1, further comprising a tongue arranged on the leaf spring or established by the leaf spring, the tongue being inserted into the slot-shaped recess, wherein the tongue projects into a toe region of the prosthetic foot.

12. The prosthetic foot as claimed in claim 1, wherein a separate insertion element is arranged in a forefoot region of the foot casing, the insertion element having a rigidity that is different from a rigidity of the foot casing or a rigidity of the receiving portion.

13. The prosthetic foot as claimed in claim 1, wherein a forefoot region of the foot casing has a different stiffness as compared to the rest of the foot casing.

14. The prosthetic foot as claimed in claim 1, wherein the foot casing has an insertion element extending into a forefoot region of the foot casing.

15. The prosthetic foot as claimed in claim 1, wherein at least one of the receiving portion and the core is removably attached to the foot casing.

16. The prosthetic foot as claimed in claim 1, wherein the receiving portion is formed as a separate piece from the foot casing and the core.

17. The prosthetic foot as claimed in claim 1, wherein the foot casing has the appearance of a human foot.

18. The prosthetic foot as claimed in claim 1, wherein the receiving portion is removable from the cavity of the foot casing.

19. The prosthetic foot as claimed in claim 1, wherein the core, receiving portion and foot casing each comprise different materials.

20. The prosthetic foot as claimed in claim 1, further comprising a void positioned between a top side of the leaf spring and an inner surface of the foot casing, the void extending from the proximal fastening device to the receiving portion.

21. The prosthetic foot as claimed in claim 1, wherein receiving portion is secured to the casing with a form fit connection.

22. A prosthetic foot, comprising:
a core having a leaf spring, a heel cushion, and a tongue, the tongue extending from a distal end portion of the leaf spring or established by a frontal end portion of the leaf spring, the heel cushion comprising a foam material and being positioned along a bottom side of the leaf spring, the leaf spring projecting in an anterior direction from the heel cushion, the heel cushion extending into a forefoot of the prosthetic foot;
a proximal fastening device configured to secure the prosthetic foot to a below knee tube or a below knee shank;
a foot casing defining a cavity;
a receiving portion having a slot-shaped recess sized to removably receive the tongue to permit interchanging of the receiving portion relative to the core, the receiving portion extending anteriorly beyond the tongue, the receiving portion and core being removably insertable in the cavity with the tongue inserted into the slot-shaped recess to permit interchanging of the core and receiving portion relative to the foot casing.

23. The prosthetic foot as claimed in claim 22, wherein the receiving portion fills a forefoot region of the foot casing.

24. The prosthetic foot as claimed in claim 23, wherein the receiving portion comprises a material with a different stiffness than material of the foot casing.

25. The prosthetic foot as claimed in claim 22, wherein the core is secured to the foot casing in a heel region using a form fit connection.

26. A prosthetic foot, comprising:
a core comprising a leaf spring and a heel cushion, the heel cushion positioned along a bottom side of the leaf spring, and the heel cushion extends over at least two thirds of a length of the prosthetic foot from a heel end of the leaf spring toward a frontal end portion of the leaf spring;
a proximal fastening device configured to secure the prosthetic foot to a below knee tube or a below knee shank;
a foot casing having a cavity;
a receiving portion having a pre-formed slot-shaped recess and extending anteriorly beyond the frontal end portion of the leaf spring;
a tongue arranged on the leaf spring or established by the leaf spring, and removably inserted into the slot-shaped recess to permit interchanging of the receiving portion relative to the core;
wherein the receiving portion with the tongue inserted into the slot-shaped recess is insertable into and removable from the cavity of the foot casing to permit interchanging of the core and receiving portion relative to the foot casing.

27. The prosthetic foot of claim 26, wherein the leaf spring projects in an anterior direction from the heel cushion.

28. The prosthetic foot of claim 27, wherein the heel cushion extends over about three fourths of a length of the leaf spring.

29. A prosthetic foot, comprising:
a core comprising a leaf spring and a heel cushion, the leaf spring having a top side, a bottom side, a heel end portion, and a frontal end portion, the heel cushion positioned along the bottom side of the leaf spring from the heel end portion of the leaf spring into a forefoot of the prosthetic foot;
a proximal fastening device configured to secure the prosthetic foot to a below knee tube or a below knee shank;
a foot casing having a cavity;
a receiving portion having a slot-shaped recess sized to removably receive the frontal end portion of the leaf spring to permit interchanging of the receiving portion relative to the core and extending anteriorly beyond the frontal end portion of the leaf spring, the receiving portion comprising a different material than the foot casing;
wherein the receiving portion with the leaf spring inserted into the slot-shaped recess is removably insertable into the cavity of the foot casing to permit interchanging of the core and receiving portion relative to the foot casing.

30. The prosthetic foot as claimed in claim 29, wherein the core is secured to the foot casing with a form fit element in a heel region.

31. The prosthetic foot as claimed in claim 30, wherein the form fit element includes a groove formed in the heel cushion and a projection extending from an interior surface of the foot casing into the groove.

* * * * *